United States Patent [19]
McKee, Jr.

[11] Patent Number: 4,998,068
[45] Date of Patent: Mar. 5, 1991

[54] BIAS CURRENT CONTROL FOR PROVIDING ACCURATE POTENTIOMETRIC MEASUREMENTS

[75] Inventor: Charles B. McKee, Jr., Fort Collins, Colo.

[73] Assignee: In-Situ, Inc., Laramie, Wyo.

[21] Appl. No.: 352,770

[22] Filed: May 16, 1989

[51] Int. Cl.⁵ ............................................ G01N 27/46
[52] U.S. Cl. .............................. 324/438; 307/272.3; 340/870.04; 324/601
[58] Field of Search ................ 204/400, 1 T, 401; 307/272.3; 330/2, 51; 324/438, 601; 340/870.04

[56] References Cited

U.S. PATENT DOCUMENTS

| | | | |
|---|---|---|---|
| 3,568,085 | 3/1971 | Pimenoff | 330/51 |
| 3,988,689 | 10/1976 | Ochi | 330/51 |

FOREIGN PATENT DOCUMENTS

| | | | |
|---|---|---|---|
| 1197170 | 11/1959 | France | 324/438 |
| 0212008 | 11/1984 | Japan | 330/51 |
| 44526 | 6/1961 | Poland | 324/438 |
| 1138518 | 1/1969 | United Kingdom | 324/438 |

Primary Examiner—Reinhard J. Eisenzopf
Assistant Examiner—Jose M. Solis
Attorney, Agent, or Firm—Sheridan, Ross & McIntosh

[57] ABSTRACT

Apparatus and method are provided to ensure accuracy of a measurement signal obtained using a potentiometric sensor placed in a solution. The apparatus includes an interface amplifier that generates a relatively large turn-on bias current whenever the amplifier is initially powered on. To avoid polarization of the potentiometric sensor by the turn-on bias current, a switch device is used to direct the turn-on bias current along a path away from the potentiometric sensor. The switch device is controlled using a timer circuit that causes a change in position of the switch device after a predetermined time delay. During the time delay, the bias current reduces to a normal value and polarization of the potentiometric sensor has been avoided. An accurate measurement of a physical parameter associated with the solution can then be taken without the detrimental effect of the turn-on bias current on the potentiometric sensor. The apparatus has particular utility in obtaining water quality data, such as hydrogen potential, specific ion potential and oxygen reduction potential.

24 Claims, 1 Drawing Sheet

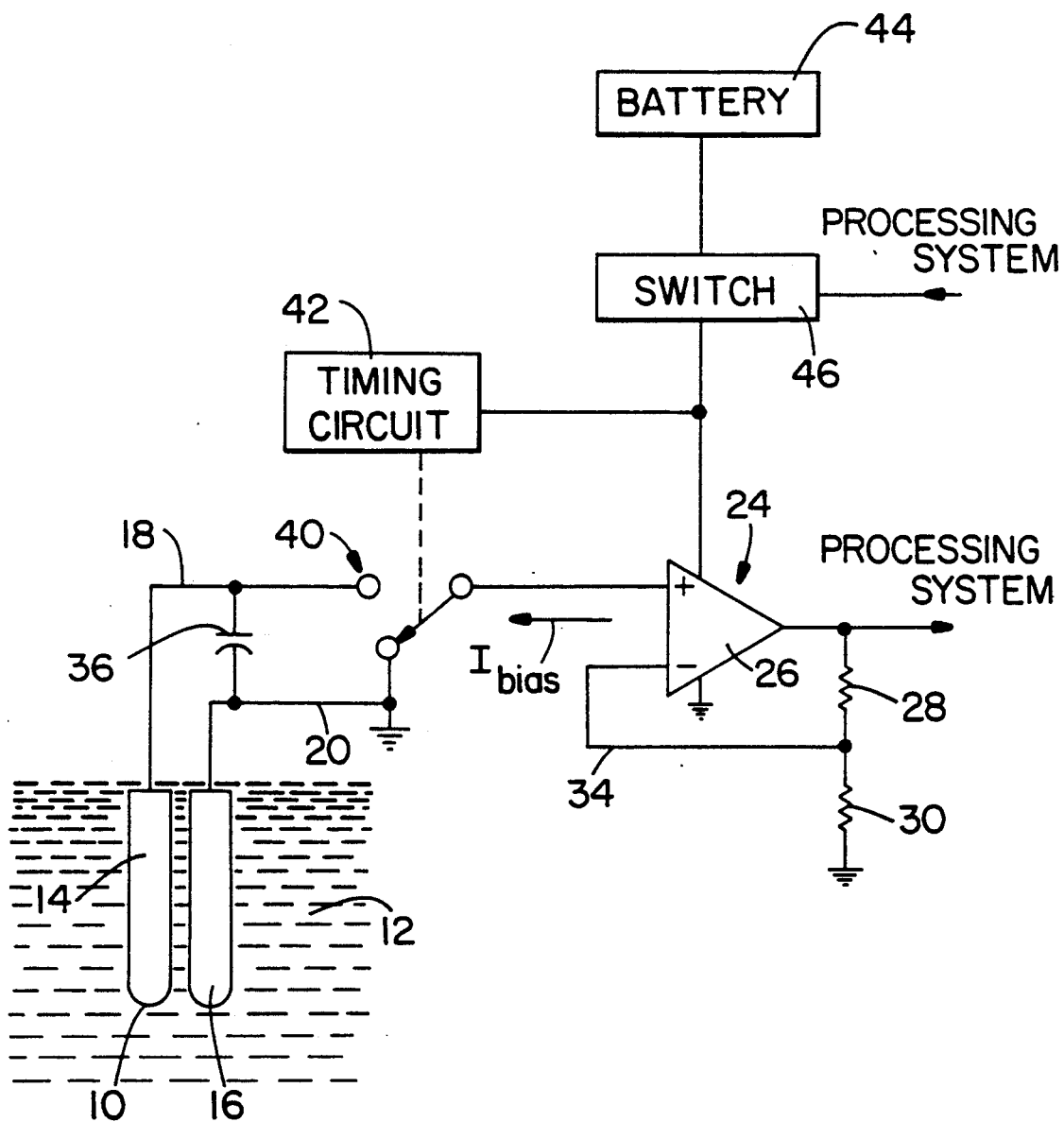

BIAS CURRENT CONTROL FOR PROVIDING ACCURATE POTENTIOMETRIC MEASUREMENTS

FIELD OF THE INVENTION

The present invention relates to an apparatus for taking measurements of physical parameters and particularly to taking measurements using a potentiometric sensor located in a solution while avoiding inaccuracies due to bias currents that could polarize the sensor when power is applied to the apparatus.

BACKGROUND OF THE INVENTION

It is often desirable to be able to obtain information directed to the quality or physical characteristics of a solution. In one application, it is worthwhile to obtain water quality data for surface and/or ground water environments. Such data might include hydrogen potential (pH), specific ion potential (pIon) and oxygen reduction potential (ORP), and other information of that nature. In connection with obtaining such data, potentiometric sensors can be used to measure the data. Potentiometric sensors are a class of sensors with characteristically high source impedances (in the range of about $10^8$ ohms) and which measure galvanic potential based on the chemical activity in the solution.

In connection with developing a measurement signal representative of the physical parameter using the potentiometric sensor, interface amplifiers are available for amplifying the measurement signal and which have input impedances of $10^{13}$ ohms or greater and bias currents of $10^{-12}$ amperes or less. A high input impedance is required for the interface amplifier because of the high source impedance of the potentiometric sensor. It is also important that bias currents be minimal to avoid polarizing the solution in the vicinity of the potentiometric sensor. Polarization occurs when a direct current is applied to the solution at a rate greater than the ion migration rate within the solution. Polarization causes a cloud of ions of opposite polarity to form about the potentiometric sensor. Because of such ion formation, the measurement signal would have a value different from the true or actual value of the physical parameter of the solution being measured.

Typically, potentiometric measurements are made in laboratory environments in which the measuring instrument or equipment power is applied prior to taking measurements and a "warm-up" time of 5-10 minutes does not detrimentally impact system performance. Such a warm-up period would result in the stabilization of the potentiometric sensor wherein any polarization thereof, which would affect the accuracy of the measurement signal, would be dissipated and no longer present. Recently, however, newer developments of instrumentation involving potentiometric sensors have evolved where such instruments are battery powered. Such instruments include potentiometric sensors that are located in the field or in an environment in which the sensor or equipment need only be powered on for a short time interval within which to obtain the measurement and then is powered down for the remaining time. In such a case, it is detrimental to system performance, particularly battery life, to require or utilize a warm-up period of 5-10 minutes. Such a warm-up period would result in an unacceptable drain on the battery energy and no accurate and useful measurement would be obtainable during this warm-up period.

SUMMARY OF THE INVENTION

An apparatus is provided for eliminating, or at least substantially reducing, polarization of the potentiometric sensor utilized in providing a measurement signal. This is accomplished by controlling the path of bias current generated when the apparatus is powered on.

More particularly, in addition to the potentiometric sensor, the apparatus includes an interface amplifier communicating with the potentiometric sensor. The interface amplifier amplifies the measurement signal, which is obtained using the potentiometric sensor. The amplified measurement signal is an accurate analog representation of the physical parameter or parameters being measured and can then be further processed so that it is understandable to the user of the present invention. In one embodiment, such information relates to water quality data to assist the user in evaluating the characteristics of a particular water supply or reservoir.

With regard to insuring the accuracy of the measurement signal, the key aspect of the present invention involves the control of bias currents that are generated when the apparatus is initially turned on. That is, it has been observed that, when the apparatus is first powered on, a turn-on bias current is generated which is several orders of magnitude larger than the normal bias current of the amplifier. Such a bias current tends to polarize the potentiometric sensor. If such polarization is permitted to occur and insufficient time is allowed to elapse after such polarization has occurred and before the measurement signal is obtained, an inaccurate measurement signal results. More specifically, the turn-on bias current introduces inaccuracies into the measurement signal whereby the measurement signal does not accurately reflect the actual or true value of the physical parameter being measured. Instead of the potentiometric sensor providing a signal that is accurately indicative of the physical parameter present in the solution, it outputs a signal that has been affected by the polarization of the potentiometric sensor due to the turn-on bias current.

Upon recognition of this problem relating to the turn-on bias current, a solution was devised to eliminate or reduce its effect by diverting or re-routing the path taken by the turn-on bias current. Rather than permitting the turn-on bias current to flow to the potentiometric sensor and thereby polarize the same, another current path is provided whereby the turn-on bias current does not communicate with the potentiometric sensor. In that regard, the present invention further includes a switch device having first and second positions or states. In the first position, the switch device directs the turn-on bias current along the desired, alternative path so that the turn-on bias current does not polarize the potentiometric sensor. In the second position, the measurement signal provided by the potentiometric sensor communicates with the interface amplifier. A timer circuit communicates with the switch device to control the same. When the apparatus is initially powered on, the switch device is in its first position. After a predetermined interval of time or delay, the timer circuit causes the switch device to be changed to its second position so that an accurate measurement can be obtained. Consequently, particularly when a battery is utilized, the apparatus is powered down until such time that the user wishes to obtain a measurement signal. When it is desirable or advantageous to obtain a measurement signal, the apparatus is powered on; however, the switch device and timer circuit do not permit the turn-on bias current to polarize the potentiometric sensor. After the delay during which the bias current has reduced to its normal value, the timer circuit controls the switch device so that the apparatus is now able to obtain an accurate measurement signal. The delay is relatively short, a matter of seconds, so that essentially no warm-up time of the apparatus is required and the apparatus is powered on for only a relatively short amount of time, a matter of seconds, during which time the accurate measurement signal is obtained. After obtaining the measurement signal, the apparatus can once again be turned off until the user decides to obtain another measurement of the physical parameter.

Based on the foregoing summary, a number of salient features of the present invention are immediately recognized. An apparatus is provided for controlling turn-on bias current generated in an amplifier so that a potentiometric sensor disposed in a solution is not polarized. As a result, accurate measurement signals are obtained. Virtually no warm-up time is required to use the apparatus after it has been powered on. This is particularly important when the source of power is a battery whereby the battery life can be preserved. Relatedly, the battery-powered apparatus can be more easily or conveniently used in a field environment in which the potentiometric sensor is placed in position for taking measurements at selected intervals of time. Such a capability enables the apparatus to be particularly useful in measuring water quality data obtainable from both surface and below ground water environments.

Additional advantages of the present invention will become readily apparent from the following discussion particularly when taken in conjunction with the accompanying drawing.

BRIEF DESCRIPTION OF THE DRAWING

The sole FIGURE of the present invention schematically illustrates the hardware for obtaining the measurement signal, together with the turn-on bias current control for preventing, or at least reducing, polarization of the potentiometric sensor.

DETAILED DESCRIPTION

In accordance with the present invention, an apparatus is provided for use in obtaining measurements of a physical parameter. The physical parameter is preferably associated with a solution. In one main application, the solution includes water and the physical parameter being measured includes hydrogen potential (pH), specific ion potential (pIon) or oxygen reduction potential (ORP). Such water-related data is of value in informing the user of the apparatus about underground or surface water quality or characteristics. Based on water quality data, determinations can be made by the user concerning important attributes associated with the water.

With reference to the sole figure, the apparatus includes a transducer device 10 for measuring a physical parameter of the solution 12 and outputting a measurement signal. The measurement signal is an electrical signal whose amplitude represents the value or magnitude of the physical parameter being measured. In the preferred embodiment, the transducer device 10 is a potentiometric sensor, which is able to output an accurate measurement signal within seconds of power application to the measurement circuitry. Potentiometric sensors typically have high source impedances ($10^8$ ohm) and measure galvanic potential in a solution due to chemical activity therein. In the embodiment illustrated in the figure, the potentiometric sensor is a dual probe device, which is capable of measuring the hydrogen potential (pH) of the solution 12. That is, the transducer device 10 includes a first or measurement probe 14 and a reference probe 16. In some configurations the measuring probe 14 and the reference probe 16 are physically packaged together as a combination probe. The physical parameter associated with the solution 12 can be measured due to the potential difference between the two probes 14, 16. In the case where the physical parameter is hydrogen potential, the potential difference between the two probes 14, 16 results in the generation of a measurement signal outputted by the measurement probe 14 to be carried by the measurement signal conducting line 18 for further processing. The reference probe 16 is typically in electrical communication with a common or ground line 20. The measurement signal conducting line 18 and the common line 20 are part of a cable connected to the potentiometric sensor 10.

The apparatus also includes an interface amplifier circuit 24. The interface amplifier circuit 24 includes an amplifier 26 which communicates with the potentiometric sensor 10. Specifically, the measurement signal conducting line 18 is electrically connectable to the non-inverting input of the amplifier 26. In the embodiment illustrated, the interface amplifier circuit 24 also includes first and second gain resistors 28, 30. The first gain resistor 28 is connected to the output of the amplifier 26 while the second gain resistor 30 is connected to the first gain resistor 28 at one side and to the common or ground line at its opposite side. Feedback to the amplifier 26 is provided by the feedback line 34, which electrically connects the junction of the first and second gain resistors 28, 30 and the inverting input of the amplifier 26. In the preferred embodiment, the resistance values of the gain resistors are chosen to provide the usually desired amplifier gain associated with the interface amplifier circuit 24. The gain of the amplifier circuit is determined by the relationship: Gain = 1 + first gain resistor 28/second gain resistor 30.

It should be understood that various and other amplifier circuits could be employed other than the particular amplifier circuit 24 illustrated in the figure. It is important that the amplifier circuit 24, however, have a high input impedance because of the high source impedance of the potentiometric sensor 10. Such interface amplifiers 26 typically have an input impedance of $10^{13}$ ohms or greater, with normal bias currents of $10^{-12}$ amperes or less. A bias current is generated when the amplifier 26 is powered on, which bias current flows in the conducting line 18 between the non-inverting input of the amplifier 26 and the potentiometric sensor 10. The actual direction of bias current flow will depend on the characteristics of amplifier 26. The bias current is identified in the figure as $I_{bias}$.

With regard to powering on the amplifier 26, during experimentation using the apparatus, it was observed that a turn-on bias current in the microampere range was initially generated before this current stabilized to the nanoampere or picoampere range. The relatively high bias current, in the microampere range, was not expected and the turn-on bias current was maintained at that level during the initial several milliseconds after application of power to the amplifier 26. This observation relating to turn-on bias current was noted in both monolithic and hybrid types of amplifiers. It was also noted that the rate or slope of the power supply application appeared to have little or no effect on the generation of the turn-on bias current in the microampere range. It was further observed that, when insufficient stabilizing or settling time was utilized after powering on the amplifier 26, inaccurate measurement signals were being provided by the potentiometric sensor 10 and outputted by the amplifier 26. If, on the other hand, sufficient time was permitted to elapse before taking a measurement after powering on the amplifier 26, a measurement signal accurately representing the value of the physical parameter being measured in the solution 12 was obtained.

The conclusion reached as a result of the investigations and experiments was that the initial pulse of amplifier bias current was polarizing the potentiometric sensor 10 or that it was charging a stray capacitor, or a combination thereof. The capacitor 36 represents stray circuitry capacitance including capacitance associated with the cable carrying the measurement signal. The high source impedance of the potentiometric sensor 10, in conjunction with cable and stray circuitry capacitance 36, create time constants of a magnitude that can require 1–5 minutes for the measurement signal to stabilize to a final, accurate value, after the polarization effect, due to the turn-on bias current, has dissipated.

In the preferred embodiment, because it is beneficial that the apparatus, particularly the amplifier 26, be battery powered, it is not satisfactory to permit or require that the apparatus have a relatively long warm-up period, after power is applied to the amplifier 26. If such were the case, there would be relatively extensive battery energy being utilized to obtain the measurement. Consequently, a solution was sought to permit the use of battery power, while preserving or optimizing battery life. With further reference to the figure, the present invention includes further circuit hardware for controlling or directing the bias current so that it does not flow to the potentiometric sensor 10 and cannot cause polarization thereof.

More specifically, the apparatus includes a switch device 40 having at least two positions or states. In a first position of the switch device 40, that portion of the conducting line 18 connected to the non-inverting input of the amplifier 26 is electrically connected to a common or ground line. In this position, the non-inverting input of the amplifier 26 is not electrically connected to the potentiometric sensor 10 and therefore any bias current that flows from the amplifier 26 towards the potentiometric sensor 10 would not be able to continue along that path; rather, any such bias current is routed to a common or ground line using the switch device 40. The first position of the switch device 40 is illustrated in the figure. With respect to the second position of the switch device 40, a current path is provided between the potentiometric sensor 10 and the non-inverting input of the amplifier 26. In this position, the measurement signal from the potentiometric sensor 10 electrically communicates with the amplifier 26.

To achieve the major objective of the present invention, when the apparatus, particularly the amplifier 26, is powered on, the switch device 40 is in the first position whereby any bias current from the amplifier 26 passes to the common or ground line by means of the first position of the switch device 40. After the bias current has dissipated, or at least substantially dissipated, the switch device 40 can then be caused to change to its second position whereby a measurement signal can be obtained. With regard to changing the position of the switch device 40 from its first position to a second position, the apparatus also includes a timing circuit 42, which electrically communicates with the switch device 40. The timing circuit 42 monitors time and, after the passage of a predetermined time interval, triggers the changing of the switch device 40 from its first position to its second position. In one embodiment, the switch device 40 is a relay which includes an electrical coil that, when energized by the timing circuit 42, causes the switch to change position. When the electrical coil is de-energized, the switch position changes back to its first or original state. In a similar embodiment, the relay could be a latching relay that would be pulsed to cause the switch to change positions.

With respect to providing power to the apparatus, the figure illustrates a DC battery 44 which electrically connects to the amplifier 26 through a switch 46. The switch 46 acts to prevent drain on the battery when no measurement signal is being obtained. When a measurement is being taken, the switch 46 changes state to permit the battery voltage to be applied to the amplifier 26. At the same time the amplifier 26 is turned on, the timing circuit 42 is activated to begin monitoring time, during which time the switch device 40 remains in the first position so that the turn-on bias current has a path away from the potentiometric sensor 10. At the end of the predetermined time interval, typically about 1 millisecond to several milliseconds, the timing circuit 42 causes the switch device 40 to change state whereby the measurement probe 14 once again communicates with the non-inverting input of the amplifier 26.

In conjunction with applying the battery power from the battery 44 to the amplifier 26, a separate system, such as a processing system, electrically communicates with the switch 46. The user is able to control the position of the switch 46 using the processing system so that the switch 46 only permits the application of power to the amplifier 26 when a measurement is being taken.

In operation, the apparatus is normally powered off and in this state, the switch device 40 is normally in the first position. Consequently, when the apparatus is first turned on so that the battery 44 applies power to the amplifier 26 through the switch 46, the switch device 40 is in its first position. As previously noted, in this state, the bias current that is generated upon the initial application of power to the amplifier 26 flows along that portion of the conducting line 18 to the ground or common line. The bias current that is generated continues to flow along this path until it is dissipated, or at least substantially dissipated. The dissipation time corresponds to the predetermined time interval that is being monitored by the timing circuit 42. At the end of the predetermined time interval, the portion of the timing circuit 42 for controlling the state of the switch device 40 from its first position to its second position is activated. When activated, the switch device 40 is in its second position and the measurement signal from the potentiometric sensor 10 has a path to the non-inverting input of the amplifier 26. The measurement signal is amplified by the interface amplifier circuit 24 and outputted from the amplifier 26 for further processing. In one embodiment, the output of the amplifier 26 is applied to the processing system, which can process the measurement signal to present information in a form suitable and understandable to the user. In one embodiment, such a processing system is described in U.S.

patent application Ser. No. 07/150,050, filed Jan. 29, 1988, and entitled "Accurate Analog Measurement System," which application is assigned to the same assignee as the present invention.

After the desired measurement or measurements have been taken for a desired or predetermined amount of time, the switch 40 can be caused to change state whereby power is removed from the amplifier 26 and the timing circuit 42. When this occurs, the switch device 40 changes state back from the second position to the first position. The apparatus is now once again in the condition that it was in before enabling it for obtaining a measurement.

In view of the foregoing detailed description, a number of advantages of the present invention are readily seen. A battery powered apparatus is provided for obtaining measurements of physical parameters in the field. Battery life is preserved by controlling unwanted bias current so that the turn-on bias current does not polarize a potentiometric sensor resulting in an inaccurate measurement being taken, in the absence of a relatively lengthy warm-up time. As a consequence, there is no battery drain due to any need for a warm-up period before an accurate measurement signal can be obtained.

The foregoing discussion of the invention, including any variation of the preferred embodiments, has been presented for purposes of illustration and description. It is not intended that any such embodiment be exhaustive or in any way limit the invention to the precise form disclosed, and other modifications and variations may be possible in light of the above teachings. It is intended that the appended claims be construed to include other alternative embodiments of the invention except insofar as limited by the prior art.

I claim:

1. An apparatus for measuring a physical parameter associated with a solution, comprising:
   potentiometric sensor means for measuring a physical parameter associated with a solution;
   first means responsive to said potentiometric sensor means for outputting a signal relating to the physical parameter and wherein said first means generates a bias current;
   second means for powering said first means; and
   third means having a first state for automatically coupling said first means to a first potential when said second means is applied and having a second state for coupling said first means to said potentiometric sensor means wherein said coupling occurs automatically after a predetermined time following the application of said second means,
   whereby the effect of said bias current on said potentiometric sensor means is reduced.

2. An apparatus, as claimed in claim 1, wherein:
   said second means includes a DC battery.

3. An apparatus, as claimed in claim 1, wherein:
   said potentiometric sensor means includes first and second probes, with one of said probes being a reference probe.

4. An apparatus, as claimed in claim 1, wherein:
   said potentiometric sensor means includes probes for measuring hydrogen potential, specific ion potential or oxygen reduction potential.

5. An apparatus, as claimed in claim 1, wherein:
   said first means includes amplifier means for amplifying a signal received from said potentiometric sensor means.

6. An apparatus, as claimed in claim 1, wherein:
   said third means includes timer means for monitoring time from the application of power to said first means.

7. An apparatus, as claimed in claim 6, wherein:
   said switch means includes first and second positions and wherein said first means is connected to said first position when said turn-on bias current is generated by said first means.

8. An apparatus, as claimed in claim 7, wherein:
   said first potential is a substantially ground potential and said first position communicates with one of said ground potential and said potentiometric sensor means.

9. An apparatus, as claimed in claim 7, wherein:
   said second position communicates with said potentiometric sensor means.

10. An apparatus, as claimed in claim 7, wherein:
    said potentiometric sensor means includes first and second probes and wherein said second position of said switch means communicates with said first probe during the obtaining of a measurement of the physical parameter.

11. An apparatus, as claimed in claim 1, wherein:
    said third means includes switch means and means for controlling said switch means between first and second positions.

12. An apparatus, as claimed in claim 11, wherein:
    said means for controlling includes timer means for monitoring time from the application of power to said first means.

13. An apparatus, as claimed in claim 2, wherein:
    said battery is electrically connected to said first means.

14. An apparatus, as claimed in claim 1, wherein:
    said first means includes gain means including resistor means.

15. An apparatus, as claimed in claim 1, wherein:
    said potentiometric sensor means includes cable means having stray capacitance.

16. An apparatus for automatically diverting a turn-on bias current away from a potentiometric sensor, comprising:
    first means for outputting a signal relating to a physical parameter associated with a solution, wherein said first means also generates a turn-on bias current;
    means for powering said first means; and
    second means for automatically directing said turn-on bias current away from the path of the potentiometric sensor when said means for powering is applied to said first means.

17. An apparatus, as claimed in claim 16, wherein:
    said means for powering includes a DC battery, and said means for directing includes:
    timer means for monitoring the interval from the time said means for powering is applied to said first means; and
    switch means, responsive to said timer means, for automatically providing two different paths for said turn-on bias current.

18. A method for automatically avoiding inaccurate measurements using a potentiometric sensor to measure a physical parameter associated with a solution, comprising:
    providing a first signal path for turn-on bias current when power is applied to a signal outputting device;
    delaying for a time interval;

permitting turn-on bias current to flow along said first signal path;

providing a second signal path to the signal outputting device from the potentiometric sensor wherein said providing occurs automatically after said timer interval has elapsed; and obtaining a signal relating to the physical parameter using said signal outputting device.

19. A method, as claimed in claim 18, wherein:
said providing of said first signal path includes causing switch means to be automatically disposed in a first state when said power is applied.

20. A method, as claimed in claim 18, wherein:
said step of applying power includes applying DC battery power.

21. A method, as claimed in claim 18, wherein:
said step of providing said second signal path includes automatically causing switch means to be disposed in a second state.

22. A method, as claimed in claim 18, wherein:
said step of delaying includes monitoring time.

23. A method, as claimed in claim 18, wherein:
said step of obtaining a signal includes amplifying a signal from the potentiometric sensor and outputting said amplified signal.

24. An apparatus, as claimed in claim 6, wherein:
said third means includes switch means, responsive to said timer means, for coupling said first means to said first potential when said third means is in said first state and for coupling said first means to said potentiometric sensor means when said third means is in said second state.

* * * * *